United States Patent [19]
Devlin et al.

[11] Patent Number: 5,419,769
[45] Date of Patent: May 30, 1995

[54] SUCTION SYSTEMS

[75] Inventors: Thomas Devlin, Cambridge; Karl Ulrich, Belmont, both of Mass.; Frank Willis, Hancock, N.H.

[73] Assignee: Smiths Industries Medical Systems, Inc., Keene, N.H.

[21] Appl. No.: 965,843

[22] Filed: Oct. 23, 1992

[51] Int. Cl.6 .............................................. A61M 1/00
[52] U.S. Cl. .................................. 604/119; 604/118; 604/163; 604/171; 604/246; 604/264; 604/317; 604/319; 604/326; 604/902
[58] Field of Search ..................... 137/205, 907; 251/9-10; 128/763, 765, 766, 768, 770, 771; 604/65, 67, 73, 95, 100, 118, 119, 131, 149, 256-258, 317-320, 323-324, 902, 264, 161, 163, 268, 246, 247, 169, 171, 174, 176

[56] References Cited

U.S. PATENT DOCUMENTS

| | | |
|---|---|---|
| 3,780,738 | 12/1973 | Deaton . |
| 3,911,919 | 10/1975 | Raitto . |
| 3,991,762 | 11/1976 | Radford . |
| 4,036,232 | 7/1977 | Genese ........................ 128/763 |
| 4,468,216 | 8/1984 | Muto . |
| 4,502,503 | 3/1985 | Lester . |
| 4,526,573 | 7/1985 | Lester et al. . |
| 4,569,344 | 2/1986 | Palmer ........................ 604/119 |
| 4,680,026 | 7/1987 | Weightman et al. . |
| 5,236,425 | 8/1993 | Kurtz et al. ................. 604/320 |

FOREIGN PATENT DOCUMENTS 2207709  2/1989  United Kingdom .

Primary Examiner—Randall L. Green
Assistant Examiner—P. Zuttarelli
Attorney, Agent, or Firm—Pollock, Vande Sande & Priddy

[57] ABSTRACT

A medico-surgical suction system has a container with an outlet connected to a vacuum pump and an inlet connected to a suction catheter via a dual-lumen tube assembly one end of which is connected to the container and the other end of which is has a suction control and a coupling for the catheter. A valve located in the outlet of the container is connected to the suction control via a minor lumen of the tube. A side lumen enables the vacuum pump to apply reduced pressure to one end of the valve which holds the valve off against the action of a spring. Actuation of the suction control allows air to flow to the valve via the minor lumen so that the effect of the reduced pressure is overcome and the spring opens the valve.

22 Claims, 4 Drawing Sheets

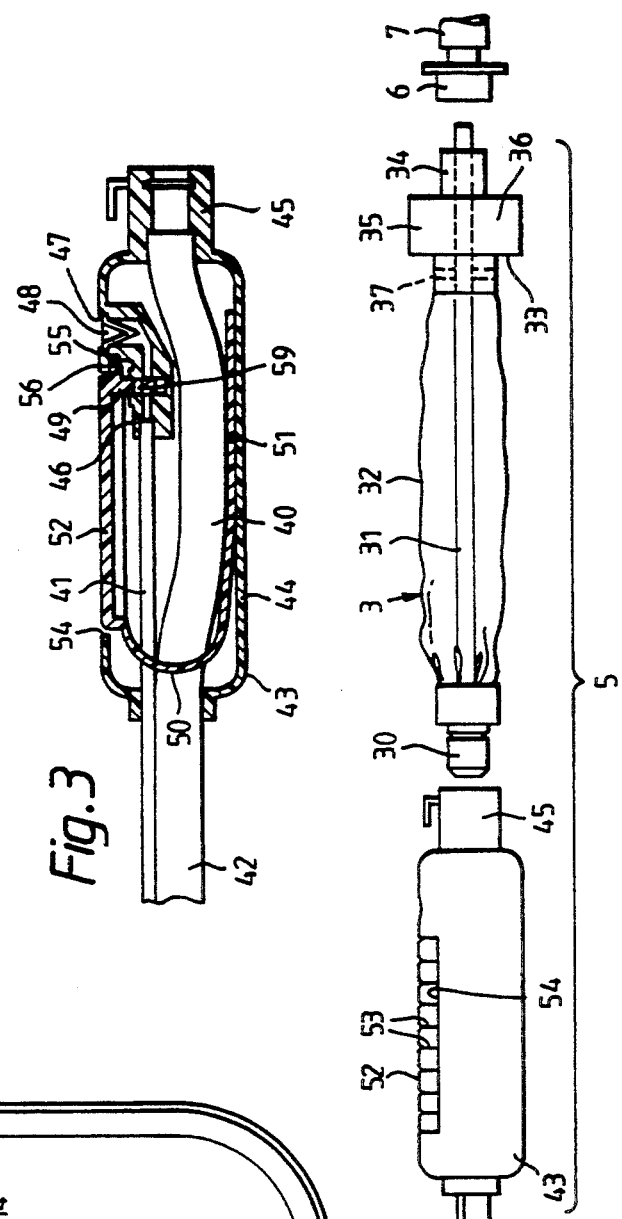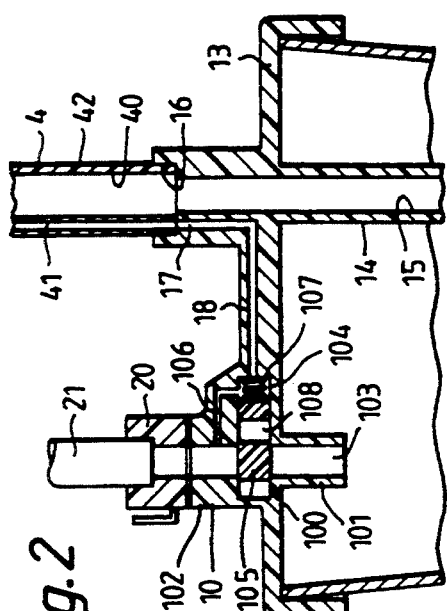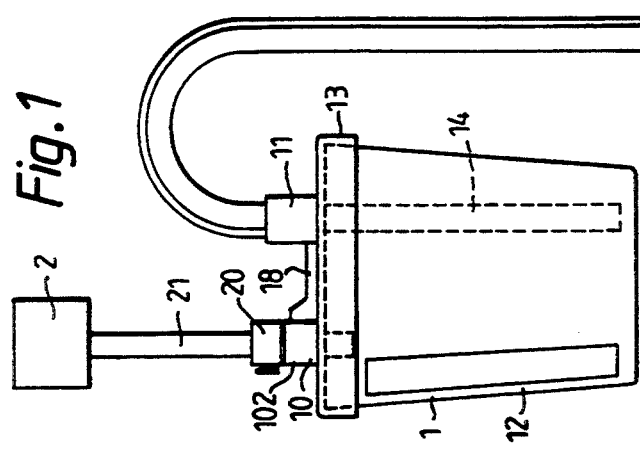

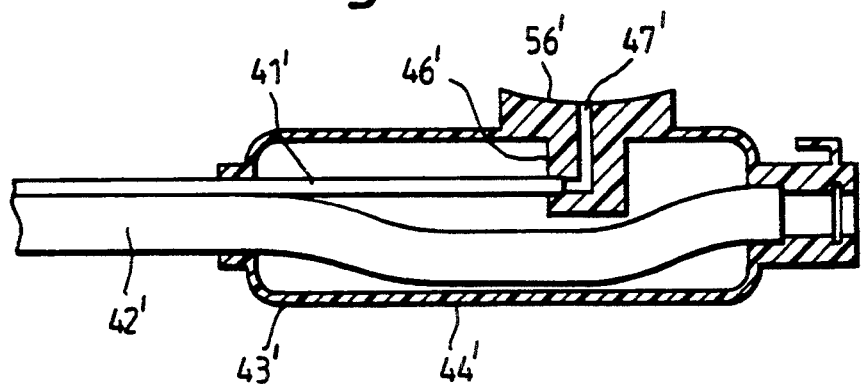
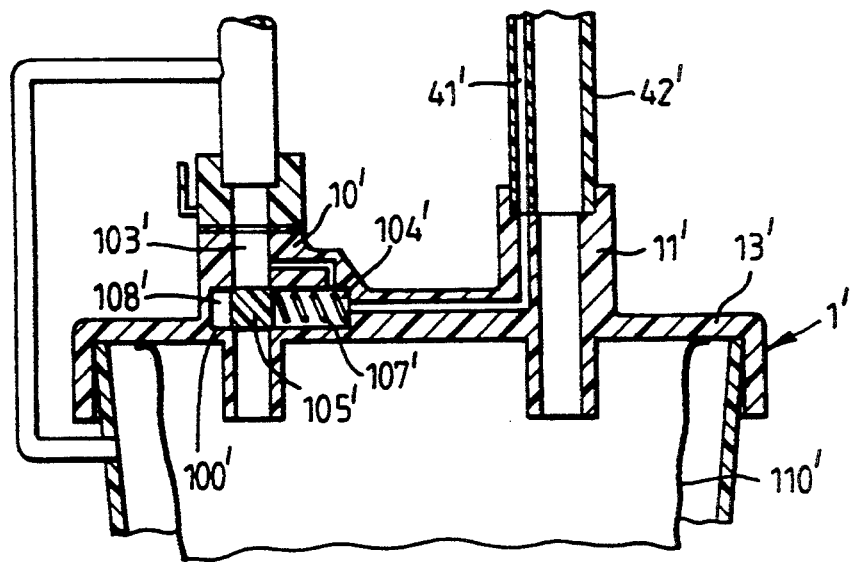

SUCTION SYSTEMS

FIELD OF THE INVENTION

This invention relates to suction systems.

The invention is more particularly concerned with medical suction systems which can be used for aspirating secretions from a patient's trachea or an artificial airway such as a tracheostomy or other tracheal tubes. The invention can also be used for removing blood and debris from surgical sites.

BACKGROUND OF THE INVENTION

Suction systems of this kind generally comprise a container and a suction catheter connected to the container inlet, the outlet of the container being connected to a vacuum pump so that a reduced pressure is created in the container which in turn applies suction to the catheter. In such systems, the vacuum pump generally operates continuously and the catheter includes a valve by which suction at the tip of the catheter can be controlled. In its simplest form, the valve comprises an aperture in the wall of the catheter which, when open, allows air to enter the catheter and thereby prevents any significant suction effect at the tip. The aperture can be closed, when desired, by the thumb of the user, or by a movable flap, so that the suction effect is confined to the tip of the catheter. The valve is located close to the patient end of the catheter so that the surgeon can control the valve with the same hand as he uses to manipulate the tip of the catheter. Examples of such catheters are described in U.S. Pat. Nos. 3,911,919 and 4,468,216. The problem with this form of valve is that the suction control aperture provides a path through which contaminated material sucked into the catheter can leak out. This is a significant disadvantage in view of the present concern about cross-infection and the transmission of infectious diseases.

In order to reduce the risk of escape of material, catheters have been made which include a sealed valve. Examples of suction catheters with a push-down spool valve are shown in U.S. Pat. Nos. 4,680,026, 4,526,573 and 4,502,508. A suction catheter with a resilient valve member is described in U.S. Pat. No. 4,569,344. Many other forms of suction catheter with different suction control valves are also known.

One problem with these valves is that, because they must have a high integrity seal to prevent escape of suction fluid externally of the device and inadvertent suctioning of the patient, the cost of the valve forms a large part of the total cost of the system. This is a particular disadvantage in a product which is disposed of after use on one patient. Another problem is that there can be a risk of blockage in the valve, especially where the catheter is used for suctioning of fluid containing thick tenacious mucous, tissue debris or blood clots. Currently-available valves form an integral part of the suction system and are specified for 24 hour use on a single patient. The valves cannot be re-used because this would involve re-use of the system as a whole and the attendant risk of cross-infection.

BRIEF SUMMARY OF THE PRESENT INVENTION

It is an object of the present invention to provide systems that can be used to alleviate the above-mentioned problems.

According to one aspect of the present invention there is provided a suction system comprising a suction container having an inlet and outlet, a vacuum source connected to the outlet of the container, a suction inlet assembly connected to the inlet of the container and valve means including a valve member that is displaceable between an open state in which suction is applied by the suction inlet assembly and a closed state in which no substantial suction is applied by the suction inlet assembly, the valve means including means urging the valve member to one of the open and closed states, a side lumen connecting the suction source with the valve means which is operable to apply a reduced pressure to said valve member and urge it to the other of the open and closed states, and control means controlling the application of reduced pressure to the valve member such as to control the valve means.

The valve means is preferably located adjacent the suction container, at the outlet of the suction container. The means urging the valve member to one of the open and closed states may be a spring. The control means is preferably located remote from the valve means, the suction inlet assembly including a control lumen extending from the control means to the valve means, and the control means including an orifice that can be opened and closed by the user to control entry of air into the control lumen and thereby control the application of reduced pressure to the valve member. The means urging the valve member may urge the valve member to an open state, the side lumen being connected to apply suction to urge the valve member to a closed state, and the control means having a normally closed orifice which can be opened to allow air into the side lumen so as to reduce the effect of the reduced pressure on the valve member and allow the valve member to be displaced to an open state. The control means may include an acoustic device in the orifice which sounds when the orifice is open and suction is applied to the suction inlet assembly.

Alternatively, the means urging the valve member may urge the valve member to a closed state, the side lumen being connected to apply reduced pressure to urge the valve member to an open state, and the control means having a normally open orifice which can be closed to prevent air entering the side lumen so as to enable a reduced pressure to be applied on the valve member and thereby allow the valve member to be displaced by the reduced pressure to an open state. The valve means may include a recess along which the valve member is displaceable, the side lumen opening into one end of the recess such that reduced pressure applied by the vacuum source via the side lumen urges the valve member to the one end of the recess, and a control lumen extending from the control means and opening into the one end of the valve recess.

According to another aspect of the present invention there is provided a suction system comprising a suction container having an inlet and outlet, a vacuum source connected to the outlet of the container, a suction inlet assembly connected at one end to the inlet of the container and valve means that is operable to control suction applied by the suction inlet assembly, the valve means being located adjacent the container, and the system including valve control means located remote from the valve means towards the other end of the suction inlet assembly, and means connecting the valve control means with the valve means such that operation of the valve means can be controlled remotely.

The means connecting the valve control means with the valve means may be a suction control lumen. The suction inlet assembly may include an extruded dual-lumen suction tube in which a major lumen of the tube provides a passage for suction material into the container and the said suction control lumen is provided by a minor lumen of the tube. The container may comprise a vessel with an open top and a cap assembly secured to the top of the vessel, the cap assembly including the inlet and outlet, and the valve means being incorporated in the cap assembly. The valve means may be located at the outlet of the container. The suction inlet assembly may include a suction tube assembly and a catheter assembly, one end of the suction tube assembly providing the one end of the suction inlet assembly, an opposite end of the suction tube assembly including the valve control means and a first coupling, and the catheter assembly including a second coupling that is removably connected with the first coupling. The suction container may include a flexible liner within the container, the inlet opening into the liner.

According to a further aspect of the present invention there is provided a medico-surgical suction system comprising: a suction container having an inlet and outlet; a vacuum source; vacuum tubing connecting the vacuum source with the container outlet; a suction tube assembly having first and second ends; means connecting the first end of suction tube assembly with the container inlet; a first coupling on the second end of the suction tube assembly; a suction catheter assembly having first and second ends; a second coupling on the first end of the suction catheer that is removably engageable with the first coupling on the second end of the suction tube; and manually operable suction control means on the second end of the suction tube assembly by which suction applied at the second end of the suction catheter can be controlled such that the suction catheter can be provided without the interposition of any valve.

The first coupling on the suction tube assembly may be a female coupling, the second coupling on the suction catheter assembly being a male coupling that is insertable within the first coupling. The suction catheter assembly may include an aspiration catheter that extends from the second coupling, a flexible envelope that extends from the second coupling around the outside of the aspiration catheter, and a third coupling adapted to mate with a tracheal tube, the flexible envelope being joined with the third coupling, and the aspiration catheter being advancable through the third coupling into the tracheal tube. The third coupling preferably includes two side ports adapted for connection to a ventilation system. The container outlet may include a fourth coupling and the vacuum tubing include a fifth coupling that is removably connected with the fourth coupling, the first coupling being engageable with the fourth coupling after removal of the fifth coupling.

According to yet another aspect of the present invention there is provided a suction catheter assembly of the kind comprising a flexible aspiration catheter having a distal end and a proximal end, a valve for controlling fluid flow through the catheter, a patient connecting member for coupling the assembly to a tracheal tube, the patient connecting member having a siliding seal with the aspirating catheter which allows the catheter to be advanced into the tracheal tube, and a flexible protective envelope extending from the patient connecting member about the catheter, the improvement wherein the patient connecting member has manually actuable means for controlling the valve such that suction applied to the catheter can be controlled close to the point at which the catheter is introduced to the tracheal tube. A suction system including a suction catheter assembly, in accordance with the present invention, will now be described, by way of example, with reference to the accompanying drawings.

BRIEF DESCRIPTION OF THE DRAWINGS

FIG. 1 shows one form of the system;

FIG. 2 is a sectional side elevation view of a part of the container shown in FIG. 1 to an enlarged scale;

FIG. 3 is a sectional side elevation view of the suction control shown in FIG. 1 to an enlarged scale;

FIG. 4 is a sectional side elevation view of an alternative suction control;

FIG. 5 is a sectional side elevation view of a part of an alternative container used with the suction control of FIG. 4;

DETAILED DESCRIPTION OF THE PREFERRED EMBODIMENTS

Figure 6:
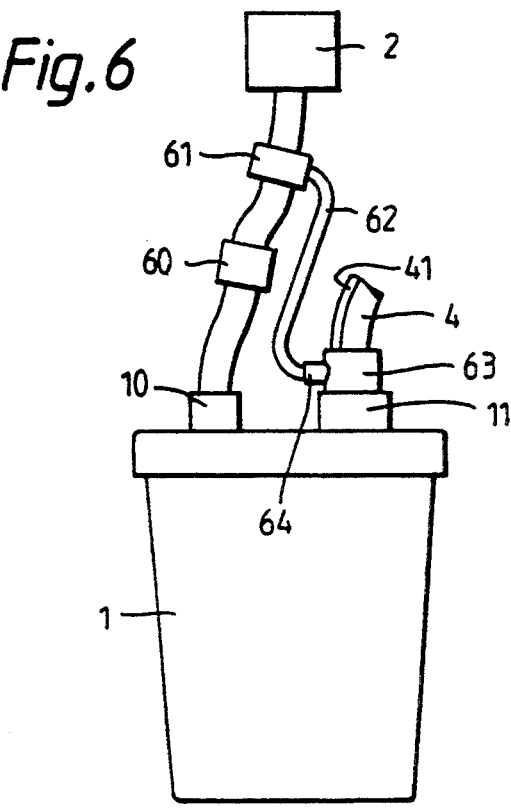
FIG. 6 is a side elevation view of a part of a further alternative system.

With reference first to FIGS. 1 to 3, the suction system comprises a container 1, a vacuum pump 2 connected to the outlet 10 of the container, a suction catheter assembly 3 and a suction tube assembly 4 connected between the suction catheter assembly and the inlet 11 of the container.

The container 1 has a cylindrical molded plastics vessel 12 which is closed at its lower end by an integral base. The upper end of the vessel 12 is closed by a separate cap assembly 13 which is sealed to the vessel. The cap 13 assembly is molded from plastics and includes integrally within it, the inlet 11 and outlet 10 of the container. The inlet 11 comprises a vertical spigot 14 which, at its lower end, projects downwardly close to the base of the container 1. A main inlet bore 15 extends through the spigot 14 which, at its lower end opens into the container 1, and at its upper end, communicates with a major lumen 40 through the suction tube assembly 4. The suction tube assembly 4 is permanently sealed into an annular recess 16 at the upper end of the spigot 14. In an alternative arrangement, the suction tube assembly 4 could be connected to the spigot 14 by removable couplings. Extending parallel with the inlet bore 15, within the wall of the spigot 14, is a valve control lumen 17 which communicates with a minor lumen 41 extending along the suction tube assembly 4. The valve control lumen 17 extends down along the upper part of the spigot 14 and along a conduit 18 extending between the inlet 11 and outlet 10. At its left-hand end, the lumen 17 opens into a valve 100.

The valve 100 is located within the outlet 10 of the container 1. The outlet 10 takes the form of a vertical spigot 101 which projects a short distance down into the vessel 12. At its upper end, the spigot 101 is shaped into a coupling 102 to which can be mated a cooperating coupling 20 on the end of tubing 21 extending to the vacuum pump 2. An outlet bore 103 extends along the spigot 101 and opens into the vacuum tubing 21. Extending transversely across the bore 103 within the spigot 101, is a valve recess 104 in which is located a slidable valve member 105. At its right-hand end, the valve recess 104 communicates with the control lumen 17 and with a side lumen 106 which extends to the bore 103 above the valve 100. The right-hand end of the valve recess 104 also contains a helical spring 107 which urges the valve member 105 to the left. In the position shown, the valve member 105 is in its right-hand, closed position, blocking the bore 103. When displaced to the left, an aperture 108 in the valve member 105 aligns with the bore 103 so that the valve 100 is open.

The suction tube assembly 4 comprises a flexible tube 42 extruded with two lumens namely the major, suction lumen 40 and the minor, control lumen 41 which is of smaller cross-section. The dual-lumen tube 42 may be several meters long and extends to a suction control 43 at the patient end of the assembly 4.

The suction control 43 has a plastics casing 44 within which the tube 42 is split into its two component lumens 40 and 41. That part of the tube providing the major, suction lumen 40 extends to a female coupling 45 formed at the right-hand, patient end of the casing 44. The remaining part of the tube 42, providing the control lumen 41 extends to a conduit 46 formed in the casing 44 and which opens on its surface via an orifice 47. A whistle 48 may be mounted in the orifice 47 to provide audible feedback when suctioning is in progress. In the position shown, air flow along the conduit 46 is prevented by a valve member 49 which projects into the conduit. The valve member 49 is formed at one end of U-shape resilient plastic component 50. The lower arm 51 of the component 50 rests on the inside of the casing 44 whereas the upper arm 52 is provided with ribs 53 and is exposed through an opening 54 in the casing. The resilience of the component 50 urges its two arms 51 and 52 apart, the separation of the arms being limited by engagement of the lower arm 51 with the casing 44 and by engagement of a lip 55 on the upper arm with the underside of a ledge 56 on the casing. The upper arm 52 can be pushed down, through the opening 54, to displace the valve member 49 so that an aperture 59 in the valve member aligns with the conduit 46 and the suction control 43 is thereby turned on.

The suction catheter assembly 3 includes a male machine end coupling 30 adapted to mate with the female coupling 45 on the suction control 43. A flexible aspirating tube or catheter 31 extends from the coupling 30 within an outer protective, flexible envelope 32. At the patient end of the assembly 3 there is a patient connecting member or T-coupling 33 to which the envelope 32 is joined. The T-coupling 33 has a first port 34 through which the aspirating tube 31 extends and which is shaped to mate with a coupling 6 at the end of a tracheal tube 7. The side ports 35 and 36 enable the coupling 33 to be connected in a ventilating circuit so that ventilation can take place in the usual way when suctioning is in progress. A sliding seal 37 in the coupling prevents gas flow into the envelope.

The suction catheter assembly 3 and the suction tube assembly 4 together provide a suction inlet assembly 5 of the system.

In order to effect suctioning, the pump 2 is switched on and the port 34 on the T-coupling 33 is connected to the coupling 6 on the tracheal tube 7. In its natural state, the suction control 43 is off, preventing passage of air into the control lumen 41 of the tube 42 and hence into the control lumen 17 of the container cap assembly 13. Because no air can enter the control lumen 17, and hence the right-hand end of the valve recess 104, a reduced pressure is created in the recess by the pump 2, via the side lumen 106. This reduced pressure is sufficient to overcome the force of the spring 107 and hold the valve member 105 towards the right-hand end of the valve recess 104 so that the valve 100 is held off. The vacuum pump 2 is, therefore, isolated by the valve 100 from the container 1 so that no suction is created in the suction tube assembly 4 or at the tip of the aspirating tube 31.

When suction is required, the user grips the suction control 43 and squeezes down the upper arm 52 of the resilient component 50, so that the valve member 49 is displaced down to its open position in which the aperture 59 aligns with the conduit 46. This allows air to be drawn through the orifice 47 into the conduit 46 and into the control lumen 41 of the tube 42. Air flows from the control lumen 41 of the tube 42, via the control lumen 17 in the container cap assembly 13 and into the right-hand end of the valve recess 104. The effect of the reduced pressure in the right-hand end of the recess 104 is thereby reduced and the pressure rises close to atmospheric pressure, which is too high to overcome the force of the spring 107. The spring 107 is, therefore, now free to displace the valve member 105 to the left-hand end of the recess 104 so that the aperture 108 aligns with the bore 103, thereby opening the valve 100 and allowing the vacuum pump 2 to create a reduced pressure in the container 1. This applies suction, via the major bore 40 through the tube 42, to the aspirating tube 31. The aspirating tube 31 is advanced into the tracheal tube 7 by manipulating through the envelope 32 so that secretions and other material are sucked into the aspirating tube, along the major lumen 40 of the suction tube 42 and into the container 1. The whistle 48 sounds while suctioning takes place. When the suction control 43 is released, the resilience of the component 50 displaces the valve member 49 upwardly to a closed, off position. The control lumen 17 is now sealed from atmospheric pressure and the pump 2 will create a negative pressure in the right-hand side of the valve recess 104 via the side lumen 106. This causes the valve 100 in the container 1 to close, terminating suction.

After suctioning of the tracheal tube, the aspirating tube 31 is pulled back into its envelope 32 and the assembly 3 is uncoupled from the suction control 43 for disposal. The suction tube assembly 4 can be coupled to a fresh catheter assembly 3 when it is next required for suctioning.

The suction tube assembly 4 is reused until the container 1 is full. When this happens, the vacuum tubing 21 is uncoupled from the outlet coupling 102 on the container cap assembly 13. The coupling 45 on the suction control 43 is preferably arranged so that it can be coupled onto the outlet coupling 102, thereby sealing the contents in the container 1 so that it can be disposed of in the usual way.

By locating the valve 100 remotely of its control 43, there is no risk that leakage from the valve will contaminate the user.

It will be appreciated that various modifications are possible to the invention. The suction catheter need not be a tracheal tube aspirating catheter but could be a short rigid tube used for suctioning of, for example, a surgical site. The catheter could be permanently joined with the suction control, although it is generally preferable to enable the suction catheter to be removed from the suction control so that it can be replaced more frequently. By making the suction control reusable, the suction catheter assembly itself need not have any valve and can, therefore, be made at lower cost. The use of a female coupling on the suction control reduces the risk of contact with suction substances after uncoupling the catheter assembly.

The suction control and the valve on the container could take various different forms. The valve need not be built into the top of the container but could be a separate component plugged in-line between the container outlet and the suction pump 2. FIG. 6 shows an arrangement in which a filter 60 is connected between the inlet 10 of a conventional container 1, and a valve 61 is connected between the filter and the suction pump 2. A length of tubing 62 extends from a coupling 63 on the container inlet 11 which has a branch arm 64 that connects with the control lumen 41 extending along the tubing 4. The valve 61 may be the same as the valve 100 shown in FIG. 2. The valve could be located on the inlet instead of the outlet, although there is less risk of sticking of the valve if it is located on the outlet where it will not come in contact with liquid and suction debris. The consequences of leakage from the valve are also less if the valve is located on the outlet.

Figure 7:
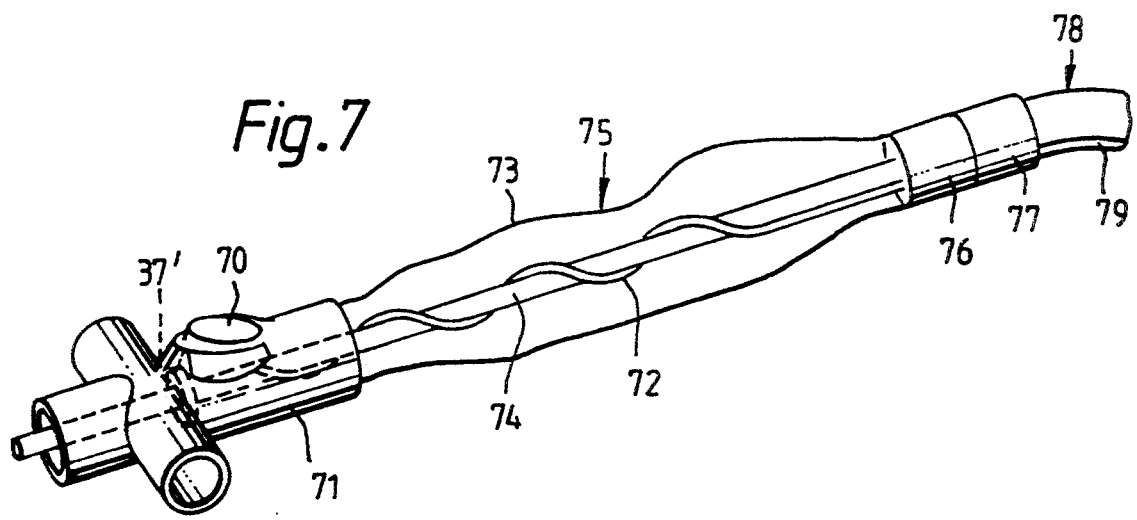
FIG. 7 is a perspective view of a part of an alternative suction catheter assembly.

The suction control valve could also be located at some other location, as shown in FIG. 7. In this arrangement, the suction control actuator 70 is located on the patient connecting member or T-coupling 71. The coupling 71 includes a sliding seal 37' with the outside of the aspirating catheter 74. A length of small bore tubing 72 extends within the flexible envelope 73, wrapped around the aspirating catheter 74. At the proximal, machine end of the suction catheter assembly 75 there is a dual coupling 76 which makes connection to a cooperating coupling 77 at the patient end of a suction tube assembly 78 so that the small bore tubing 72 connected to the control valve 70 is connected to the control lumen 79 of the suction tube assembly by means of the couplings 76 and 77. This arrangement enables the user to control suction at a point very close to where the aspiratory tube is inserted into the tracheal tube.

Figure 8:
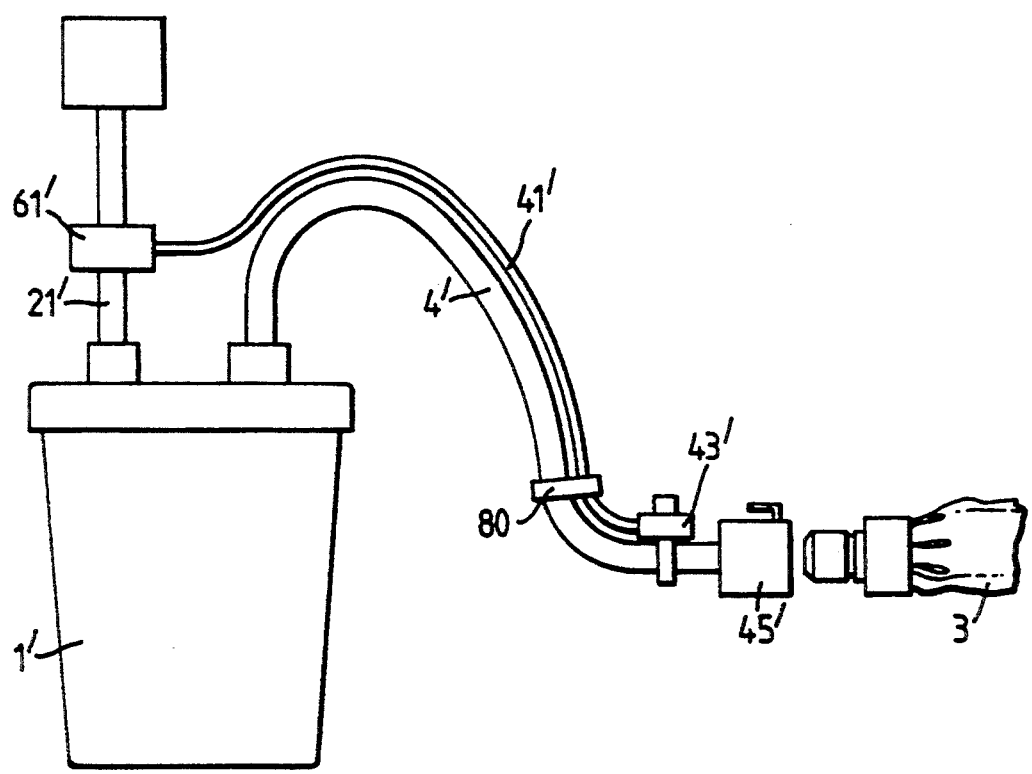
FIG. 8 is a side elevation view of a part of another alternative system.

In the arrangement of FIG. 8, the valve 61' and the suction control 43' are independent of the tubing 4' so that the tubing can be disposed of periodically and the valve reused. The suction control 43' is clipped onto the tubing 4' close to the coupling 45' which connects with the suction catheter assembly 3. The suction control lumen 41' which connects the suction control 43' to the valve 61' is independent of the tubing 4' but is clipped to it during use by one or more releasable clips 80. The valve 61 is connected in the vacuum tubing 21' so that the container 1', tubing 4' and suction catheter assembly 3 can all be disposed of while retaining the valve, its control 43' and the connecting control lumen 41' for reuse.

With reference to FIGS. 4 and 5, there is shown an alternative suction control 43' and valve 100' on the container 1'. In the suction control 43' the control lumen 41' of the suction tubing 42' is connected to a conduit 46' which opens through an orifice 47' without the interruption of any valve. The surface of the casing 44' around the orifice 47' is provided with a shallow concave recess 56' on which the user's finger or thumb is rested to cover the orifice. The valve 100' is similar to that shown in FIG. 2 and differs only in the construction the valve member 105' and its mode of operation. In particular, the valve member 105' differs from the earlier described valve member 105 in that its through aperture 108' is located at the left-hand end of the valve member so that the bore 103' is closed when the valve member 105' is located at the left-hand end of the recess 104'. In its rest position, with the orifice 47' in the suction control 43' exposed, the right-hand end of the valve recess 104' is close to atmospheric pressure; the spring 107' is in its expanded state, forcing the valve member 105' to the left-hand end of the recess 104'. The bore 103' is, therefore, blocked and the vacuum pump is isolated from the container 1'.

When the user places his finger or thumb on the recess 56' of the suction control 43', it covers the orifice 47' and prevents air entering the control lumen 41'. This allows the vacuum pump 2 to reduce the pressure at the right-hand end of the valve recess 104' which in turn causes the valve member 105' to be displaced to the right along the recess, compressing the spring 107'. In its right-hand position, the aperture 108' in the valve member 105' is aligned with the bore 103' so that the valve 100' is opened and the vacuum pump is connected to the interior of the container 1'.

Various other forms of valve are possible, for example, it might be desirable in some circumstances to use a valve which is completely sealed against the escape of liquid. Such a valve could take the form of a continuous fluid passageway which is deformable to prevent flow through it.

The container may take various different forms. For example, the container might have a flexible liner 110' such as of the kind described in GB 2207709 or U.S. Pat. No. 3,780,738 and as illustrated in FIG. 5. In this arrangement, the inlet 11' of the cap assembly 13' communicates with the interior of the liner 110' whereas the outlet 10' communicates with the space in the container 1' outside the liner 110'. In such an arrangement, the cap assembly 13' with the liner 110' attached can be disposed of and the vessel reused.

Where the container does not have a liner, the outlet may be provided with a safety valve to prevent overfilling, and a filter to prevent passage of airborne bacterial or aerosol droplets to the vacuum pump.

What we claim is:

1. In a suction system comprising a suction container having an inlet and outlet, a vacuum source connected to the outlet of the container; a suction inlet assembly connected to the inlet of the container, valve means and means for connecting the valve means between the vacuum source and the suction inlet assembly, said valve means including a valve member that is displaceable between an open state in which suction is applied by the suction inlet assembly and a closed state in which no substantial suction is applied by the suction inlet assembly, the improvement wherein said valve means includes means for urging the valve member to one of the open and closed states, a side lumen connecting the vacuum source with said valve means which is operable to apply a reduced pressure to said valve member and to urge it to the other of the open and closed states, and manual control means controlling application of reduced pressure to said valve member to selectively control the valve means.

2. A suction system according to claim 1, wherein the means urging the valve member to one of the open and closed states is a spring.

3. A suction system according to claim 1, wherein said control means is located remote from the valve means, wherein the suction inlet assembly includes a control lumen extending from the control means and to the valve means, wherein the control means includes an orifice that can be opened and closed by the user to control entry of air into the control lumen to thereby control the application of reduced pressure to the valve member.

4. A suction system according to claim 1, wherein said means for urging the valve member urges the valve member to a closed state, wherein the side lumen is connected to apply reduced pressure to urge the valve member to an open state, and wherein the control means has a normally open orifice which can be closed to prevent air entering the side lumen so as to enable a reduced pressure to be applied on the valve member and thereby allow the valve member to be displaced by the reduced pressure to an open state.

5. A suction system according to claim 1, wherein the valve means includes a recess along which the valve member is displaceable, wherein the side lumen opens into one end of the recess such that reduced pressure applied by the vacuum source via the side lumen urges the valve member to said one end of the recess, and wherein a control lumen extends from the control means and opens into said one end of the valve recess.

6. A suction system according to claim 1, wherein the valve means is located adjacent the suction container.

7. A suction system according to claim 6, wherein the valve means is located at the outlet of the suction container.

8. A suction system according to claim 1, wherein said means urging the valve member urges the valve member to an open state, wherein the side lumen is connected to apply suction to urge the valve member to a closed state, and wherein the control means has a normally closed orifice which can be opened to allow air into a bypass lumen so as to reduce the effect of the reduced pressure on the valve member and allow the valve member to be displaced to an open state.

9. A suction system according to claim 8, wherein the control means includes an acoustic device in the orifice which sounds when the orifice is open and suction is applied to the suction inlet assembly.

10. In a suction system comprising a suction container having two openings providing an inlet and outlet, a vacuum source connected to the outlet of the container, a suction inlet assembly connected at one end to the inlet of the container and valve means that is operable to control suction applied by the suction inlet assembly, the improvement wherein the valve means is connected to one of the openings adjacent the container, and wherein the system includes valve control means located remote from the valve means towards the other end of the suction inlet assembly, and means connecting the valve control means with the valve means so that operation of the valve means can be controlled remotely.

11. A suction system according to claim 10, wherein the container comprises a vessel with an open top and a cap assembly secured to the top of the vessel, wherein the cap assembly includes said inlet and outlet, and wherein the valve means is incorporated in said cap assembly.

12. A suction system according to claim 10, wherein the valve means is located at the outlet of the container.

13. A suction system according to claim 10, wherein the suction inlet assembly includes a suction tube assembly and a catheter assembly, wherein one end of said suction tube assembly provides said one end of the suction inlet assembly, wherein an opposite end of said suction tube assembly includes said valve control means and a first coupling, and wherein the catheter assembly includes a second coupling that is removably connected with the first coupling.

14. A suction system according to claim 10, wherein the suction container includes a flexible liner within the container, and wherein the inlet opens into the liner.

15. A suction system according to claim 10, wherein the means connecting the valve control means with the valve means is a suction control lumen.

16. A suction system according claim 15, wherein the suction inlet assembly includes an extruded dual-lumen suction tube in which a major lumen of the tube provides a passage for suction material into the container and said suction control lumen is provided by a minor lumen of the tube.

17. A suction system comprising:
a suction container having an inlet and outlet;
a vacuum source;
vacuum tubing connecting the vacuum source with the container outlet;
a suction tube assembly having first and second ends;
means connecting the fist end of the suction tube assembly with the container inlet;
a first coupling on the second end of the suction tube assembly;
a suction catheter assembly having first and second ends;
a second coupling on the first end of the suction catheter assembly that is removably engageable with the first coupling on the second end of the suction tube assembly; and
manually operable suction control means on the second end of the suction tube assembly, said suction control means having a manually-displaceable member that is displaceable between a first position in which it prevents suctioning at the second end of the suction tube assembly to a second position in which it enables suctioning at the second end of the suction catheter assembly such that suction applied at the second end of the suction catheter assembly can thereby be controlled and such that the suction catheter assembly can be provided without the interposition of any valve and whereby the suction catheter assembly can be disposed of separately from the suction tube assembly.

18. A suction system according to claim 17, wherein the container outlet includes a fourth coupling and the vacuum tubing includes a fifth coupling that is removably connected with the fourth coupling, and wherein the first coupling is engageable with the fourth coupling after removal of the fifth coupling.

19. A suction system according to claim 17, wherein the first coupling on the suction tube assembly is a female coupling, and wherein the second coupling on the suction catheter assembly is a male coupling that is insertable within the first coupling.

20. A suction system according to claim 17, wherein the suction catheter assembly includes an aspiration catheter that extends from the second coupling, a flexible envelope that extends from the second coupling around the outside of the aspiration catheter, and a third coupling adapted to mate with said tracheal tube, wherein the flexible envelope is joined with the third coupling, and wherein the aspiration catheter can be advanced through the third coupling into the tracheal tube.

21. A suction system according to claim 20, wherein the third coupling includes two side ports adapted for connection to a ventilation system.

22. In a suction catheter assembly of the kind comprising a flexible aspiration catheter having a distal end and a proximal end, the proximal end being adapted for connection to a suction source, a valve, means for connecting the valve between the aspiration catheter and the suction source such that the valve is operable to control fluid flow through the catheter, a tracheal tube, a patient connecting member for coupling the assembly to said tracheal tube, the patient connecting member having a sliding seal with the aspirating catheter which allows the catheter to be advanced into the tracheal tube, and a flexible protective envelope extending from the patient connecting member about the catheter, the improvement wherein the patient connecting member has manually actuable means for controlling the valve such that suction applied to the catheter can be controlled close to the point at which the catheter is introduced into the tracheal tube.

* * * * *